(12) United States Patent
Suh

(10) Patent No.: US 7,527,641 B2
(45) Date of Patent: May 5, 2009

(54) TRANSLATIONAL HINGED DOOR PLATE SYSTEM

(75) Inventor: Sean S Suh, Plymouth Meeting, PA (US)

(73) Assignee: Synthes USA, LLC, West Chester, PA (US)

( * ) Notice: Subject to any disclaimer, the term of this patent is extended or adjusted under 35 U.S.C. 154(b) by 173 days.

(21) Appl. No.: 11/078,798

(22) Filed: Mar. 11, 2005

(65) Prior Publication Data

US 2006/0217721 A1    Sep. 28, 2006

(51) Int. Cl.
*A61B 17/80* (2006.01)
(52) U.S. Cl. ...................................... 606/289
(58) Field of Classification Search ............. 606/69–71; 206/6.1, 82, 339, 347, 472–474, 487; 132/315; 220/4.22–4.23; 24/90.5, 518
See application file for complete search history.

(56) References Cited

U.S. PATENT DOCUMENTS

| | | | | | |
|---|---|---|---|---|---|
| 5,527,310 | A | * | 6/1996 | Cole et al. | 606/60 |
| 5,766,254 | A | * | 6/1998 | Gelbard | 623/17.16 |
| 6,224,602 | B1 | * | 5/2001 | Hayes | 606/69 |
| 6,235,034 | B1 | * | 5/2001 | Bray | 606/71 |
| 6,406,478 | B1 | | 6/2002 | Kuo | |
| 2003/0018335 | A1 | | 1/2003 | Michelson | |
| 2004/0034352 | A1 | | 2/2004 | Needham et al. | |
| 2005/0137597 | A1 | * | 6/2005 | Butler et al. | 606/69 |
| 2006/0287723 | A1 | * | 12/2006 | Muhanna et al. | 623/13.14 |

FOREIGN PATENT DOCUMENTS

| | | | |
|---|---|---|---|
| EP | 1520545 | A | 4/2005 |
| FR | 2863476 | A | 6/2005 |
| WO | WO 02/080789 | A | 10/2002 |

* cited by examiner

*Primary Examiner*—Eduardo C Robert
*Assistant Examiner*—Nicholas Woodall
(74) *Attorney, Agent, or Firm*—Stroock & Stroock & Lavan, LLP

(57) ABSTRACT

An assembly for use with a bone fastener includes a fixation device and a bone fastener retainer device. The fixation device has an opening configured to receive a bone fastener in an installed position in which an outer end portion of the bone fastener is located within the opening. The retainer device is receivable over the fixation device in a closed position extending over the location taken by the outer end portion of the bone fastener within the opening. Additionally, the fixation device and the retainer device together have first and second locking structures. The locking structures are configured to engage each other in an undeflected condition when the retainer device is in a partially closed position, and to snap into interlocked engagement with each other under an applied force that moves the retainer device from the partially closed position to the closed position.

18 Claims, 7 Drawing Sheets

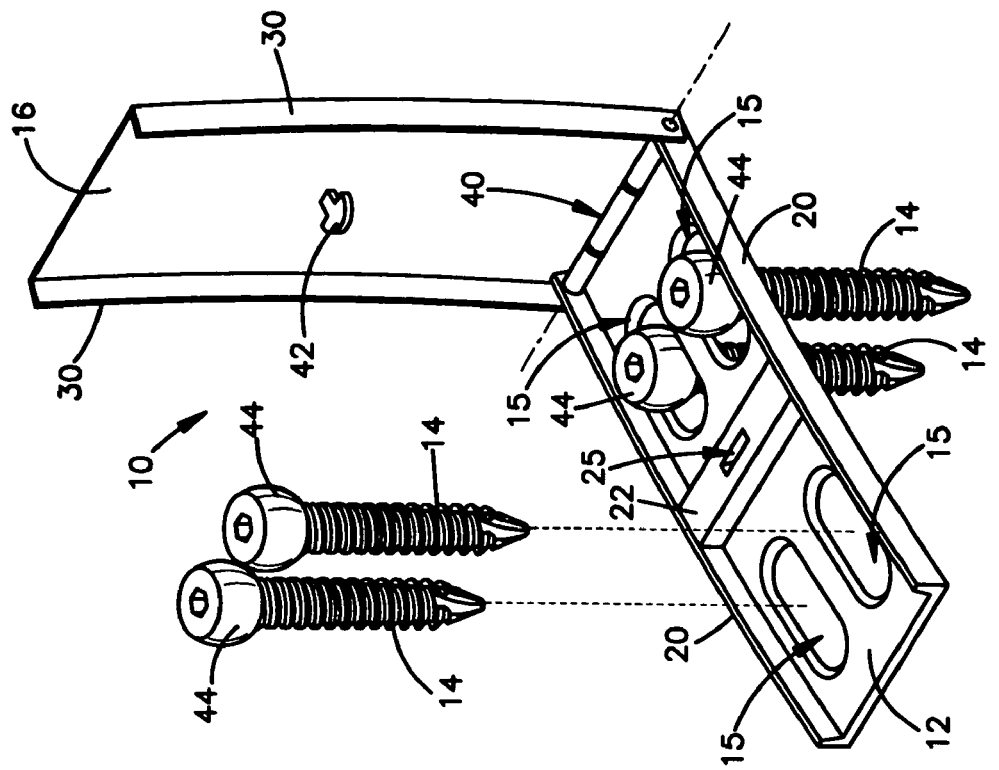
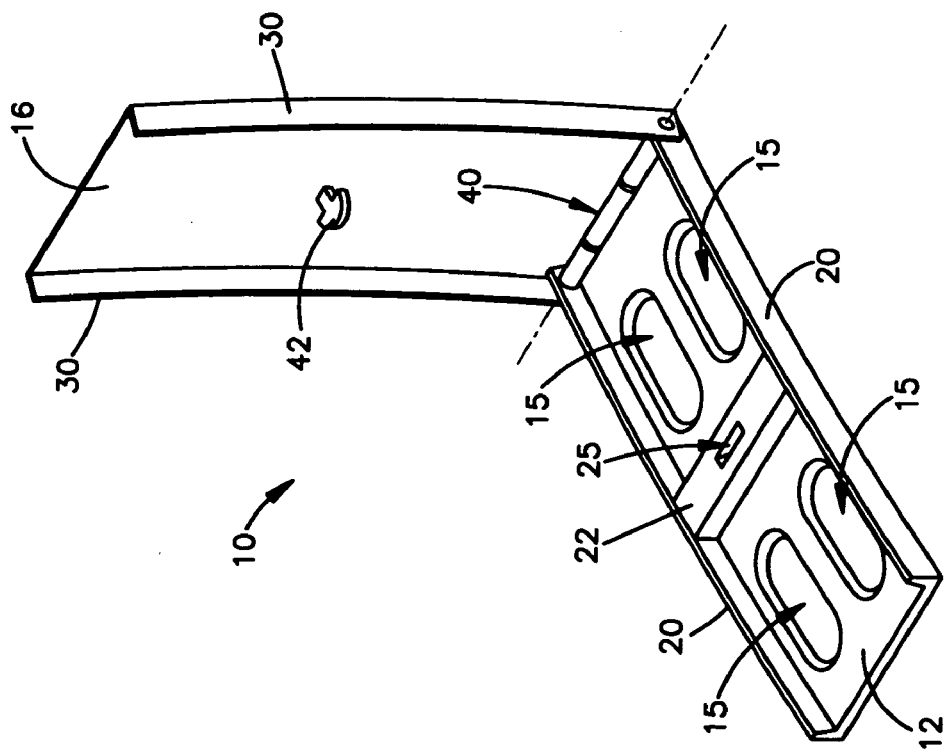

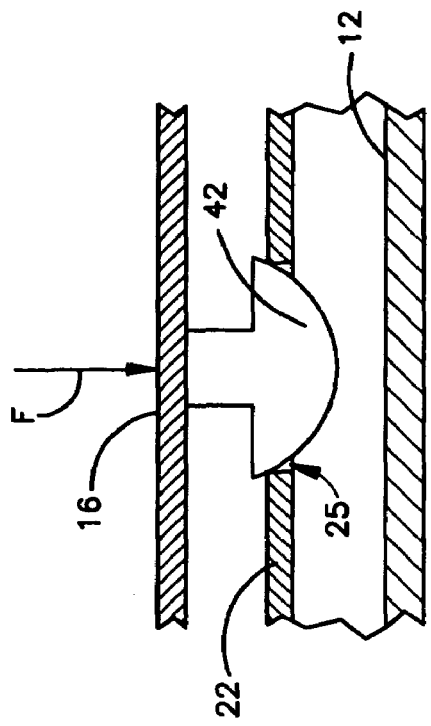
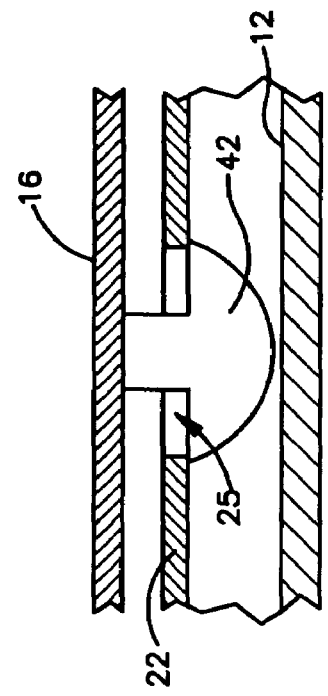
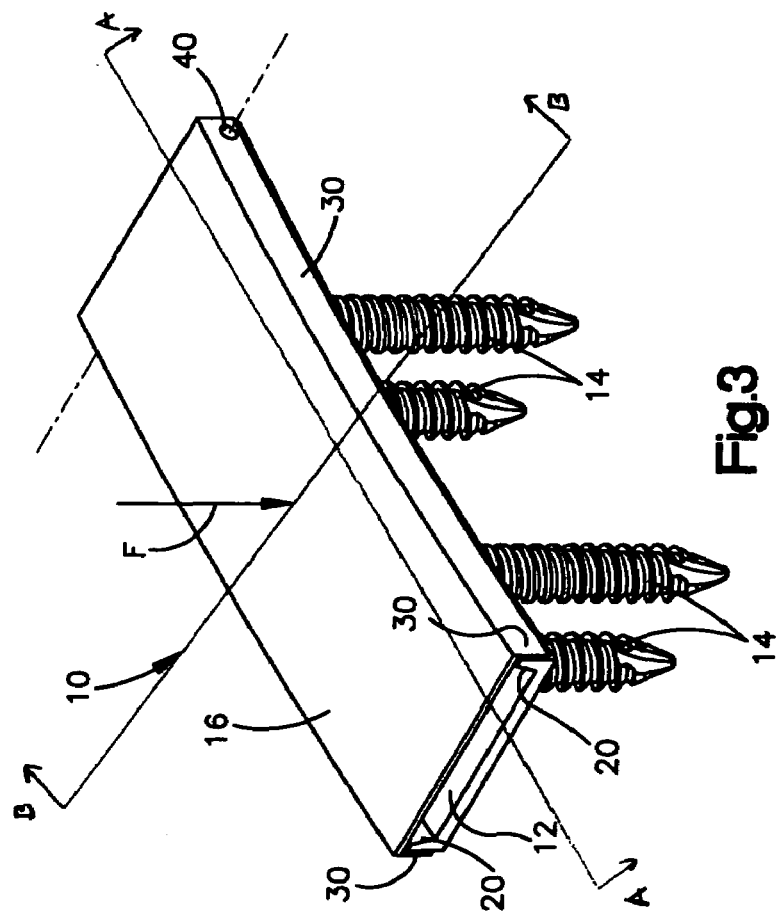

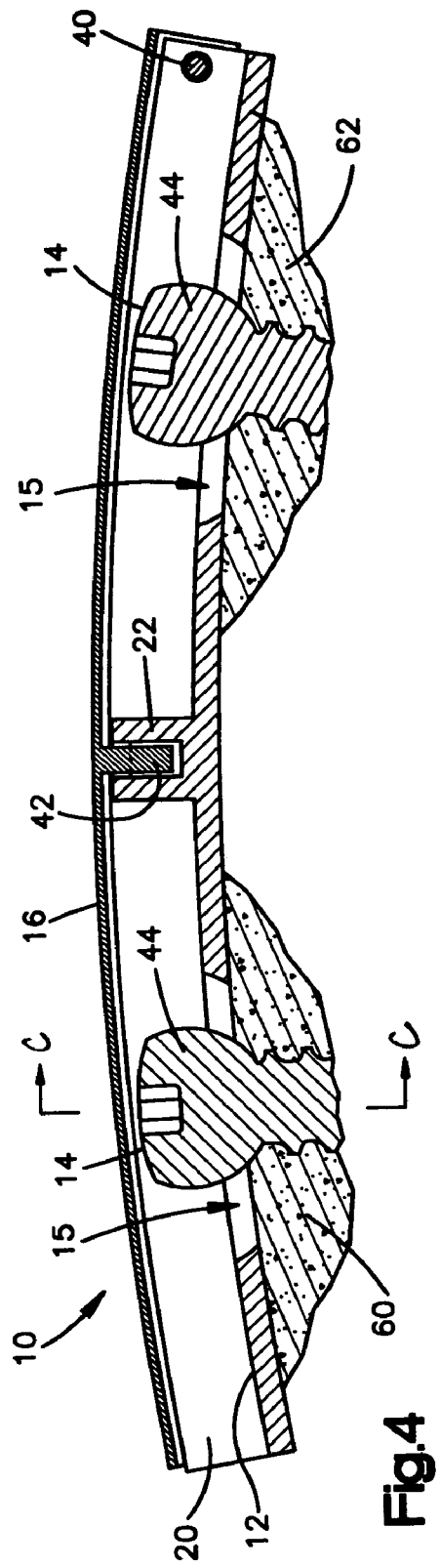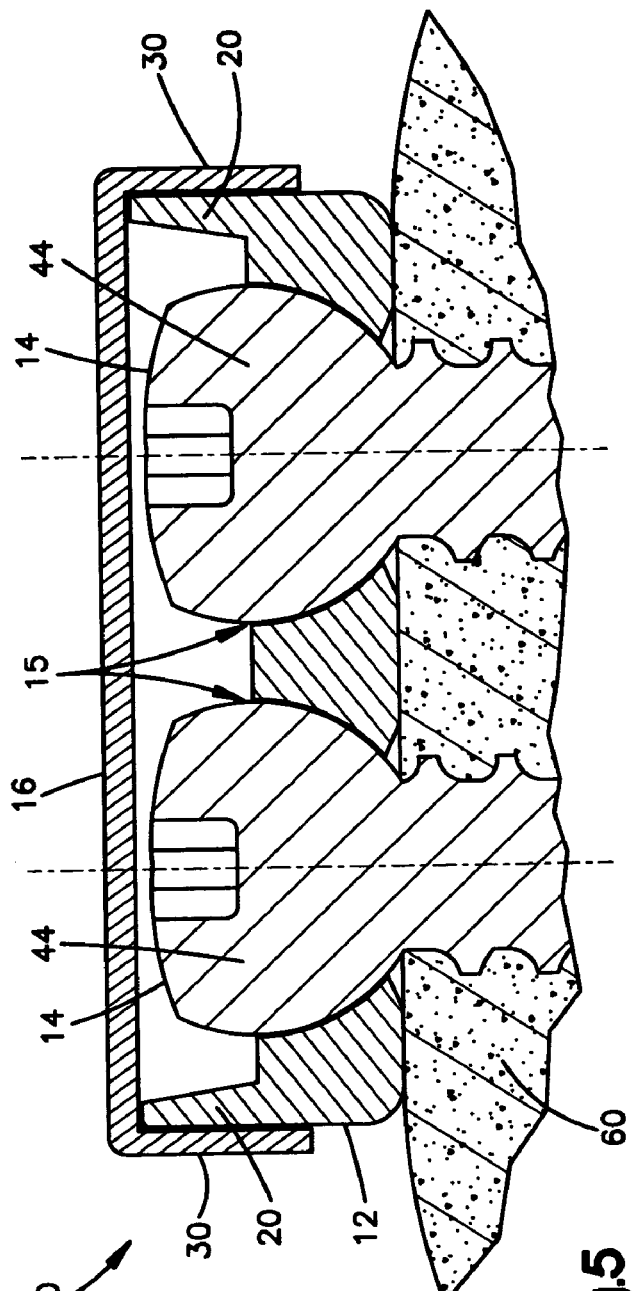

TRANSLATIONAL HINGED DOOR PLATE SYSTEM

FIELD OF THE INVENTION

The present invention is related to a fixation system. More particularly, the invention is related to a fixation system with a hinged cover plate covering at least a portion of a translational plate to prevent fastener back-out.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, polyaxial movement of fasteners through set plate hole locations only increases attachment alternatives of the fasteners themselves. The plate holes remain fixed in relation to each other and to the longitudinal axis of the plate.

Typically, a spinal fixation plate is applied to the anterior side of the affected vertebrae to span at least one affected disc space or vertebra (i.e. one in which at least a portion of the disc has been removed and a spinal fusion spacer has been inserted). The plate is fixed to the vertebrae using bone screws and acts to keep the vertebrae generally aligned during the initial period following fixation in which fusion of the spacer to the adjacent vertebrae occurs. The plate also acts to prevent the spacer from being expelled from the disc space during this initial period.

Where a spinal fusion spacer is implanted between a pair of vertebrae to be fused, the spacer rests on the endplates of the vertebrae. The outer circumference of the end plates comprises hard cortical bone and thus provides a the best surface upon which to seat the spacer. The center portion of the endplates comprises a thin cortical bone shell overlying a core of softer cancellous bone. Most, if not all, of the spacer contact surface, however, may be located in this center portion.

Subsequent to placement of the spacer, the surgeon typically compresses the disc space by pressing the adjacent vertebrae together. This compression ensures a good engagement between the spacer the endplates, increasing the chances that fusion will occur. Often in the period immediately following surgery, the spacer will subside slightly either into the under-portion of the endplates or due to graft resorption (in the case of allograft spacers).

Where a rigid fixation plate is used to connect the vertebrae, this subsidence may tend to shift more of the spinal load to the plate than is desirable. Such load shifting can also occur due to inaccuracies in installing the plate to the vertebrae. In extreme circumstances, this load shifting can result in non-fusion of the spacer to the vertebra, since firm compression between the spacer and the vertebrae is one factor contributing to successful fusion.

Accordingly, there exists a need for a fixation system which provides the desired support to the vertebrae to be fused, and which allows limited translation of the vertebrae with respect to at least a portion of the plate, thereby limiting the undesirable effects of load shielding by the plate due to graft subsidence caused by settling or normal forces experienced in the spinal column. Promoting fusion of the adjacent vertebrae is thus accomplished.

However, fasteners used with both rigid and translational plates have a tendency to back-out of their installed positions under the influence of force and movements of the spine. The back-out of the fasteners is undesirable, as the fixation assembly may shift post-operatively to an undesired location, or loosen to an undesirable level.

Hence, there is a need for a fastener retaining device can be attached to a plate to block rearward movement of the fasteners relative to the plate after the fasteners have first been placed in their installed positions on the plate.

SUMMARY OF THE INVENTION

An apparatus for use with a bone fastener includes a fixation device and a bone fastener retainer device. The fixation device has an opening configured to receive a bone fastener in an installed position in which an outer end portion of the bone fastener is located within the opening. The retainer device is receivable over the fixation device in a closed position extending over the location taken by the outer end portion of the bone fastener within the opening. Additionally, the fixation device and the retainer device together have first and second locking structures. The locking structures are configured to engage each other in an undeflected condition when the retainer device is in a partially closed position, and to snap into interlocked engagement with each other under an applied force that moves the retainer device from the partially closed position to the closed position.

Other distinct structural features of the apparatus include a hinge supporting the retainer device for movement pivotally into the closed position, and a housing that encloses the outer end portions of the bone fasteners. The housing may be defined by the fixation device and the retainer device, and may alternatively be defined by a structure that encloses the fixation device as well as the outer end portions of the bone fasteners. The housing may further enclose and support a plurality of fixation devices for movement relative to each other.

A fixation assembly for use with at least one bone fastener is described, comprising a fixation device having at least one opening configured to receive at least a portion of a bone fastener in an installed position, the at least one bone fastener having a head, wherein at least a portion of the head is located within the opening in an installed position; a bone fastener retainer device receivable over the fixation device in a closed position, wherein at least a portion of the bone fastener retainer device extends over at least a portion of the head when the fixation device is in a closed position; and wherein the fixation device further has a first locking structure, and the bone fastener retainer device further has a second locking structure, the locking structures configured to engage each other in an unlocked condition when the bone fastener retainer device is in a partially closed position, and configured to engage each other in a locked condition after an applied force shifts the bone fastener retainer device into a closed position.

The first locking structure may be a tab, and the second locking structure may be a slot, and wherein the tab is receivable in the slot. The first and second locking structures may comprise edge portions of the fixation device and the bone fastener retainer device. The edge portions may be peripheral edge portions.

The assembly may further comprise a hinge connected to the fixation device and bone fastener retainer device, wherein the hinge may be configured to pivotally shift the bone fastener retainer device into a closed position. The fixation device may be a fixation plate with a plurality of bone fastener openings, and the bone fastener retainer device may be a cover plate configured to extend over at least a portion of the bone fastener openings in the fixation device when the bone fastener retainer device is in a closed position.

The assembly may further comprise at least one additional fixation device having an opening configured to receive a bone fastener in an installed position, wherein the bone fastener retainer device is configured to fit over the openings in the fixation devices when in a closed position.

The assembly may further comprise a base supporting the fixation devices for movement relative one another. The base may include a ratchet device configured to define spaced-apart positions to which the fixation devices are movable relative to each other on the base. The base and the bone fastener retainer device may together be configured to define a housing that at least partially encloses the fixation devices when the bone fastener retainer device is in a closed position.

At least one opening may be substantially slot-shaped and has a longitudinal axis. A bone fastener may be allowed to translate along the longitudinal axis of the opening, and may be allowed to translate in situ. A bone fastener may be allowed to translate after it has been at least partially inserted into a bone segment. A bone fastener may be allowed to translate when the bone fastener retainer device is in a closed position. At least one opening may be substantially circular.

The assembly may further comprise a hinge connected to the fixation device, the hinge pivotally connected to a clamp. The clamp may be moveable between an open position and a closed position. At least a portion of the clamp may overlie at least a portion of the bone fastener retainer device when the clamp is in a closed position. At least a portion of the clamp may wrap around both the fixation device and the bone fastener retainer device when the clamp is in a closed position.

A fixation assembly for use with a bone fastener is also described, comprising a fixation device having at least one opening configured to receive at least a portion of a bone fastener in an installed position, the at least one bone fastener having a head, wherein at least a portion of the head is located within the opening in an installed position; a bone fastener retainer device receivable over the fixation device in a closed position, wherein at least a portion of the bone fastener retainer device extends over at least a portion of the head when the fixation device is in a closed position; and a first hinge connected to the fixation device and bone fastener retainer device, wherein the hinge is configured to pivotally shift the bone fastener retainer device into a closed position.

The fixation device may be a fixation plate with a plurality of bone fastener openings, and the bone fastener retainer device may be a cover plate configured to extend over at least a portion of the bone fastener openings in the fixation device when the bone fastener retainer device is in a closed position.

The assembly may further comprising at least one additional fixation device having an opening configured to receive a bone fastener in an installed position, wherein the bone fastener retainer device is configured to fit over the openings in the fixation devices when in a closed position.

The assembly may further comprise a base supporting the fixation devices for movement relative one another. The base may include a ratchet device configured to define spaced-apart positions to which the fixation devices are movable relative to each other on the base.

The assembly may further comprise a second hinge connected to the fixation device, the second hinge pivotally connected to a clamp. The clamp is moveable between an open position and a closed position. At least a portion of the clamp may overlie at least a portion of the bone fastener retainer device when the clamp is in a closed position. At least a portion of the clamp may wrap around both the fixation device and the bone fastener retainer device when the clamp is in a closed position. At least a portion of the clamp may snap-fit around at least a portion bone fastener retainer device.

The assembly may further comprise first and second ends, wherein the first hinge is located near the first end, and the second hinge is located near the second end.

A fixation assembly is also described, comprising first and second fixation devices, each having a pair of openings for use with a bone fastener; first and second bone fastener retainer devices; wherein the first bone fastener retainer device is pivotally connected to the first fixation device; and wherein the first bone fastener retainer device is pivotable into a closed position for preventing bone fastener back-out.

At least the first fixation device may have a lip, and the first bone fastener retainer device may be configured to engage the lip in a closed position. The first bone fastener retainer device may engage the lip in a snap-fit relationship.

The second bone fastener retainer device may be pivotally connected to the second fixation device, and the second bone fastener retainer device may be pivotable into a closed position for preventing bone fastener back-out. The second fixation device may have a first and second lip, and wherein the second bone fastener retainer device may be configured to engage the lips in a closed position. The second bone fastener retainer device may engage at least one lip in a snap-fit relationship.

BRIEF DESCRIPTION OF THE DRAWINGS

Preferred features of the present invention are disclosed in the accompanying drawings, wherein similar reference characters denote similar elements throughout the several views, and wherein:

FIG. 1 is a perspective view of an embodiment of a one-level bone fixation assembly with a fastener retainer device in an open position.

FIG. 2 is a perspective view of the embodiment of FIG. 1 with fasteners.

FIG. 3 is a perspective view of the embodiment of FIGS. 1-2 with the fastener retainer device in a closed position.

FIG. 4 is a cross-sectional view of the assembly of FIG. 3 taken along the line A-A, showing a pair of fasteners in adjacent vertebrae.

FIG. 5 is a partial cross-sectional view of the assembly of FIG. 4 taken on the line C-C.

FIG. 6 is a partial cross-sectional view of the assembly of FIG. 3 taken along the line B-B, just before the moment where the locking tab is fully inserted into the slot.

FIG. 7 is a partial cross-sectional view of the assembly of FIG. 3 taken along the line B-B, after the locking tab is fully inserted into the slot.

DETAILED DESCRIPTION OF THE INVENTION

Figure 8:
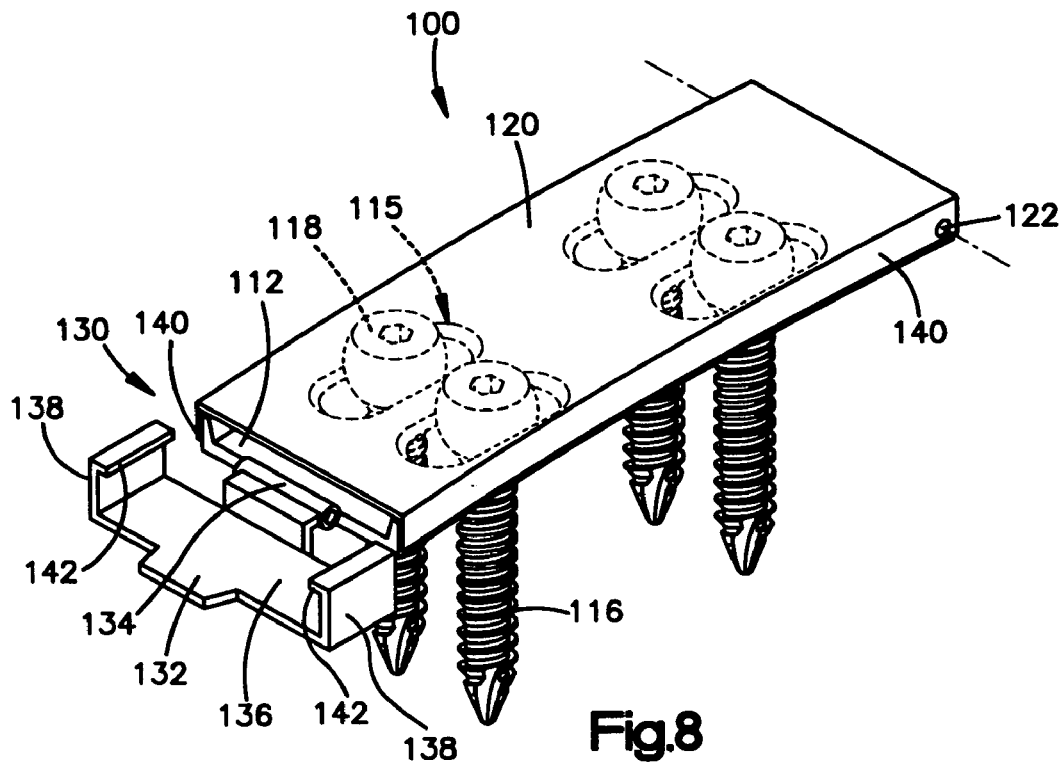
FIG. 8 is a perspective view of a second embodiment of a one-level bone fixation assembly with a fastener retainer device in a closed, unlocked position.

The plates described herein may be used in spinal fusion procedures in which a damaged or diseased disc (or part of a disc) is removed from between a pair of vertebrae and a spinal fusion spacer is placed between the vertebrae. The plates may be applied to an anterior portion of the affected vertebrae to span the affected disc space, and may be fixed to the vertebrae using bone screws. The plate may function to maintain the vertebrae aligned during the initial period following fixation in which fusion of the spacer to the adjacent vertebrae occurs. The plate may also function to share some of the axial spinal load applied to the fusion spacer to prevent extreme subsidence of the spacer into the vertebral body, such as where the patient has poor bone quality. The plates may also act to prevent the spacer from being expelled from the disc space during the initial post-operative period.

The plates may be used for single level (i.e. one-disc) or multiple-level (i.e. multiple disc) fusion procedures. Some embodiments may be used for corpectomy procedures, in which at least a portion of a vertebral body is removed. Single level plates generally may have two pairs of bone screw holes, while the multi-level plates generally may have three or more pairs of holes.

FIGS. 1-3 show an embodiment of a one-level fixation assembly 10. In this embodiment, assembly 10 includes a bone fixation plate 12 which, in this particular example, is a spinal fixation plate. A plurality of fasteners 14 may be receivable through openings 15 in the fixation plate 12 to fasten it to the spine, as shown in FIG. 2. A fastener retainer device 16 may cooperate with the fixation plate 12. In this particular example, the fastener retainer device 16 is a cover plate that fits over the fixation plate 12 in a closed position, as shown in FIG. 3. When the fasteners 14 are installed to fasten the fixation plate 12 to the spine, the cover plate 16 can be placed in the closed position to block the fasteners 14 from backing out of their installed positions relative to the fixation plate 12.

The fixation plate 12 may be configured to overlie a section of the spine to provide support that maintains the alignment of two or more vertebrae in that section of the spine. Accordingly, the fixation plate 12 may be elongated to extend between at least one pair of vertebrae. The openings 15 may be arranged in pairs adjacent to the opposite ends of the fixation plate 12 so that the pair of fasteners 14 at one pair of openings 15 can fasten the fixation plate 12 to a first vertebra and the pair of fasteners 14 at the other pair of openings 15 can fasten the fixation plate 12 to a second vertebra. Additionally, the openings 15 in each pair may be shaped as slots that are elongated lengthwise of the fixation plate 12. This may permit each pair of fasteners 14 to move vertically within the slots 15 when compression of the spine causes the two fastened vertebrae to move relatively toward each other. Slots 15 may also be fitted with captive clips (not shown) to allow fasteners 14 to move within the slots 15 and further prevent fastener 14 back-out, the details, materials, and methods of which are described in U.S. patent application Ser. No. 10/653,164 entitled "Bone Plate with Captive Clips", by Duong, et al., filed Sep. 3, 2003, the entire disclosure of which application is expressly incorporated by reference herein.

As further shown in FIG. 1, a pair of side flanges 20 may extend along the length of the fixation plate 12 between its opposite ends. A closure block 22 may be mounted on the fixation plate 12 midway between the opposite ends, and may have a slot 25. The cover plate 16 may also be elongated with a pair of side flanges 30 extending fully along its length. Moreover, the cover plate 16 may be slightly wider than the fixation plate 12 so as to fit over the fixation plate 12, as shown in FIG. 3, with the side flanges 20 on the fixation plate 12 able to be received between the side flanges 30 on the cover plate 16.

A hinge 40 may support the cover plate 16 on the fixation plate 12 for movement pivotally between the open position of FIGS. 1-2 and the closed position of FIG. 3. FIGS. 4-5 show cross-sectional views of the embodiment of FIG. 3, with the assembly 10 fastened to adjacent vertebrae 60 and 62. When the cover plate 16 is moved pivotally into the closed position, a locking tab 42 on the cover plate 16 may then be received in the slot 25 on the fixation plate 12 such that the cover plate 16 snaps into interlocked engagement with the fixation plate 12. The cover plate 16 then may extend over the outer end portions 44 of the bone screws 14 to block the bone screws 14 from backing out of the installed positions in which they fasten the fixation plate 12 to the vertebrae 60 and 62.

FIGS. 6-7 are cross-sectional views of the assembly of FIG. 3 taken along the line B-B. FIG. 6 shows the locking tab 42 just before it fully enters the slot 25, while FIG. 7 shows the locking tab 42 after it has fully entered the slot 25. The interlock between the cover plate 16 and the retainer plate 12 can be established merely by applying a force F that presses the top side of the cover plate 16 downward, as indicated schematically in FIG. 3, to push the locking tab 42 downward into the slot 25. This may cause the locking tab 42 to snap into interlocked engagement with the closure block 22. More specifically, the cover plate 16 may first be placed in a partially closed position, as shown in FIG. 6, with the locking tab 42 resting on the closure block 22. The applied force F may then cause the locking tab 42 to deflect the closure block 22 so that the edge of the locking tab 42 slides downward and snaps beneath the edges of the slot 25 to lock the cover plate 16 in the closed position, as shown in FIG. 7.

Figure 9:
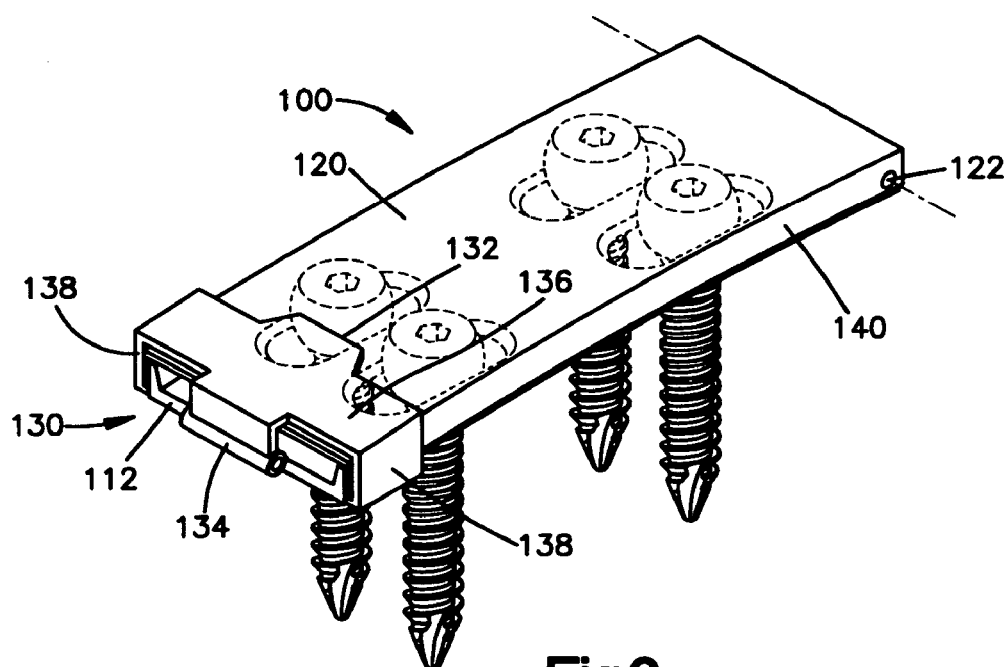
FIG. 9 is a perspective view of the assembly of FIG. 8 with a fastener retainer device in a closed, locked position.

FIGS. 8-9 show a second embodiment of a one-level bone fixation assembly 100. The fixation assembly 100 in this embodiment includes a bone fixation plate 112 with slots 115 configured to receive fasteners 116 in installed positions in which the outer end portions 118 of the fasteners 116 are located within the slots 115. The fixation assembly 100 may further include a fastener retainer device in the form of a cover plate 120 which, like the cover plate 16 described above, may be supported by a hinge 122 for movement pivotally into a closed position on the fixation plate 112. When the cover plate 120 is in the closed position, as shown in FIG. 8, it may extend over the locations taken by the outer end portions 118 of the fasteners 116 in the slots 115 to block the fasteners 116 from backing out of their installed positions on the fixation plate 112. However, the assembly 100 differs from the previously recited assembly 10 by including a locking device 130 as a substitute for the closure block 22 and locking tab 42 described above.

The locking device 130 may include a clamp 132 and a hinge 134. The hinge 134 may support the clamp 132 on the fixation plate 112 for movement pivotally into the locking position, as shown in FIG. 9. When the clamp 132 is in the locking position, a major portion 136 of the clamp 132 may extend across the adjacent end portion of the cover plate 120.

A pair of arms 138 at opposite ends of the major portion 136 may also extend downward past the side flanges 140 on the cover plate 120, and a pair of barbs 142 may project from the arms 138 beneath the fixation plate 112 to hold the clamp 132 in the locking position. The clamp 132 then may hold the closure plate 120 in the closed position. The clamp 132 should be flexible enough for the barbs 142 to spread apart and slide downward beside the flanges 140 on the cover plate 120, and to snap back toward each other beneath the fixation plate 112 as the clamp 132 is moved pivotally into the locking position.

Figure 10:
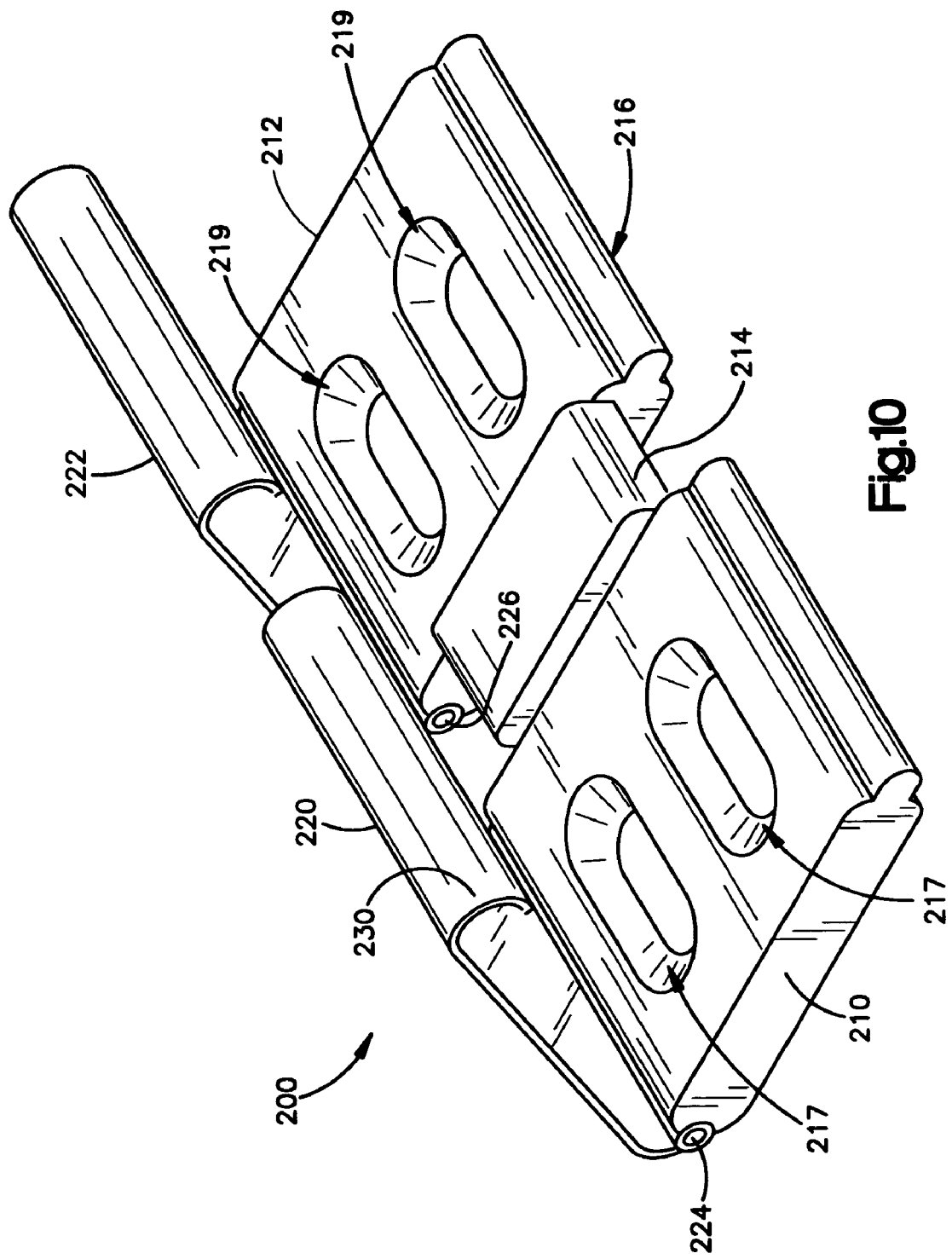
FIG. 10 is a perspective view of a third embodiment of a one-level bone fixation assembly with two fastener retainer devices in an open position.
Figure 11:
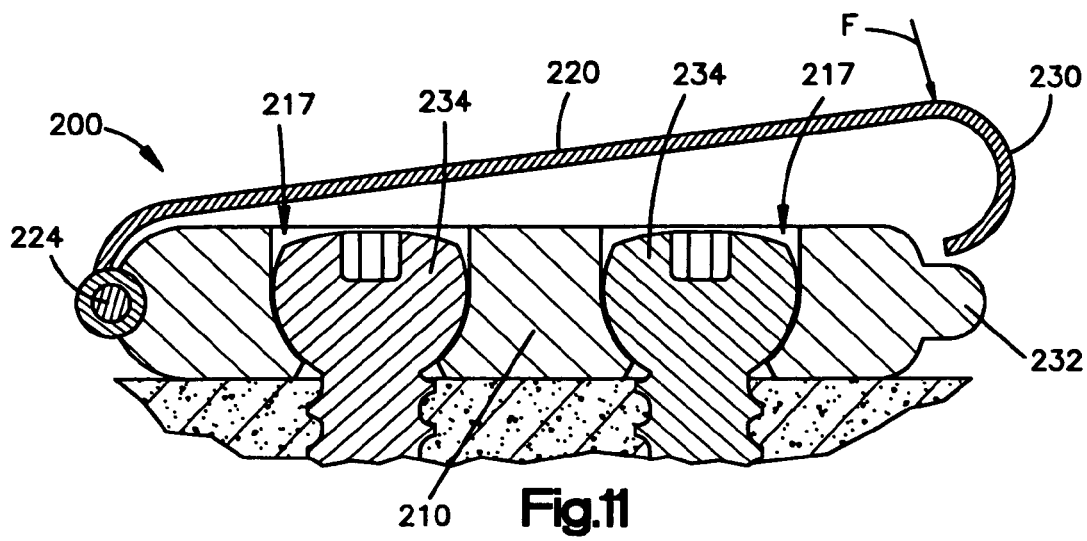
FIG. 11 is a partial cross-sectional view of the assembly of FIG. 10 with fasteners taken transversely across the assembly, with a fastener retainer device in a partially closed position, showing a pair of fasteners in a single vertebrae.
Figure 12:
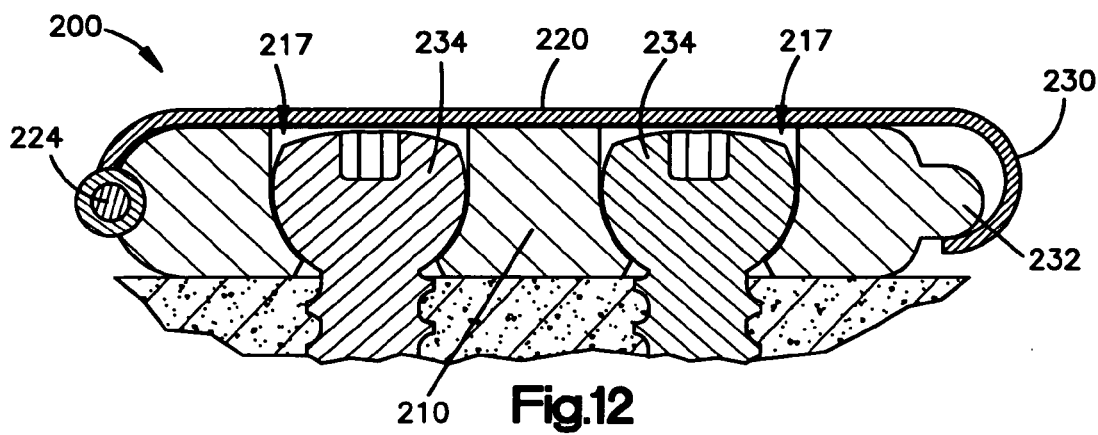
FIG. 12 is a view showing the assembly of FIG. 11 with a fastener retainer device in a fully closed position.

FIGS. 10-12 show a third embodiment of a one-level bone fixation assembly 200. In this embodiment, assembly 200 includes a pair of bone fixation plates 210 and 212. The fixation plates 210 and 212 may be joined by a connector 214 to define a single spinal fixation plate 216 with two pairs of fastener slots 217 and 219. Two fastener retainer devices 220 and 222 may be mounted on the fixation devices 210 and 212 by hinges 224 and 226, respectively, that may support them for movement pivotally into closed positions.

As shown in the embodiment of FIGS. 11 and 12, the retainer device 220 may be a cover plate with an arcuate peripheral edge portion 230 that may snap into interlocked engagement with a lip 232 at the peripheral edge of the fixation device 210. This may occur upon pivotal movement of the retainer device 220 from the partially closed position of FIG. 11 to the closed position of FIG. 12 under an applied force F. When the retainer device 220 is in the closed position, it may extend over fastener heads 234 in the slots 217 to block them from backing out of their installed positions on the fixation device 210.

Figure 13:
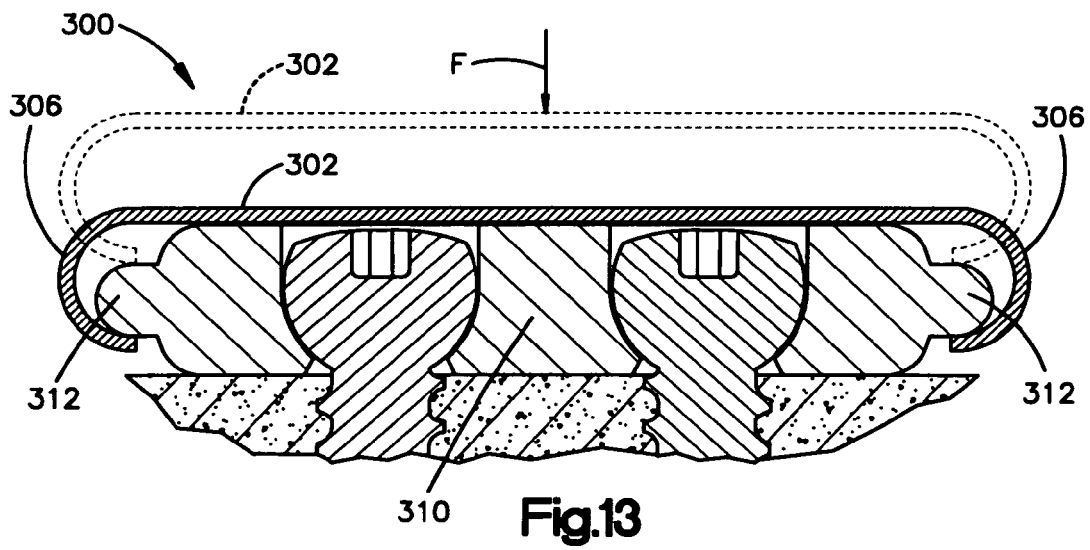
FIG. 13 is a partial cross-sectional view of a fourth embodiment of a one-level bone fixation assembly having an non-hinged fastener retainer device similar to those shown in FIGS. 10-12, lockable by a depressive force.

FIG. 13 is a fourth embodiment of a one-level bone fixation assembly 300 similar to the assembly 200 of FIGS. 10-12. The fastener retainer device 302 in this assembly 300 may have two arcuate peripheral edge portions 306, whereas the fastener retainer device 220 described above in connection with FIGS. 10-12 has a hinge 224 and a single arcuate peripheral edge portion 230. The assembly 300 may further include a bone fixation plate 310 with two corresponding lips 312, each of which may be substantially the same as the single lip 232 of FIGS. 10-11.

The retainer device 302 of FIG. 13 can be snapped into interlocked engagement with the fixation plate 310 in at least two different ways. An edge portion 306 at one side of the device 302 can first be hooked over the corresponding lip 312, and the other edge portion 306 can then be snapped pivotally over its corresponding lip 312, similar to the manner described above with reference to FIGS. 11-12. Alternatively, the retainer device 302 can first be placed on the fixation device 310 in a partially closed position in which the edge portions 306 rest on the lips 312, as shown in phantom view in FIG. 13. The edge portions 306 can then be snapped into closed positions simultaneously, as shown in full in FIG. 13, under the influence of an applied force F at the top side of the retainer device 302.

Figure 14:
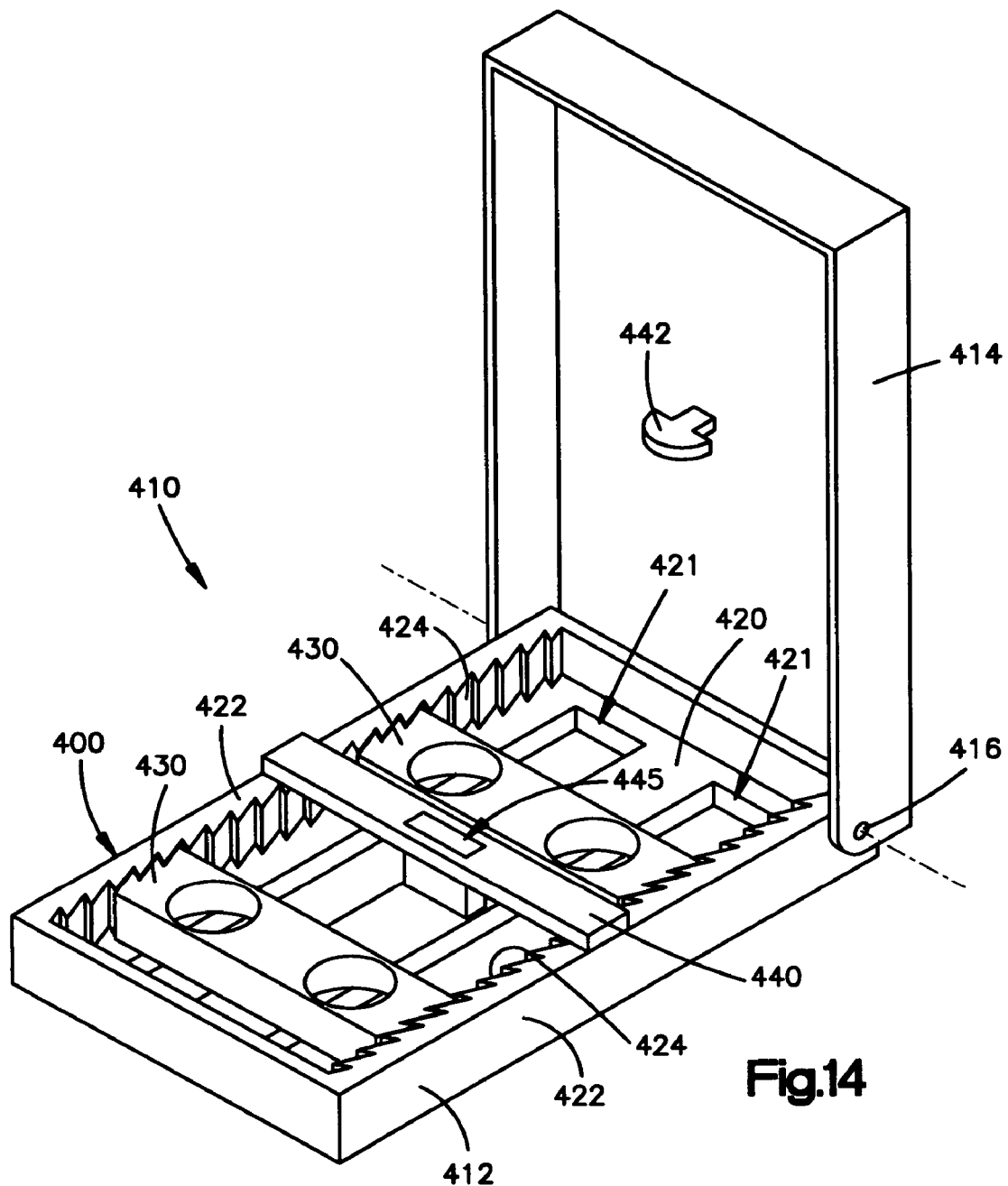
FIG. 14 is a perspective view of a fifth embodiment of a one-level bone fixation assembly with a fastener retainer device in an open position.

FIG. 14 is a fifth embodiment of a one-level bone fixation assembly 410. The housing 400 of FIG. 14 may include a base 412 and a cover 414. A hinge 416 may support the cover 414 on the base 412. In this embodiment, the base 412 is a box-shaped structure with a rectangular bottom wall 420. A pair of slots 421 may extend along the length of the bottom wall 420. The base 412 further may have a pair of opposite side walls 422 that together define a track with opposed ratchet teeth 424.

A pair of fixation blocks 430 may be supported on the side walls 424 of the base 412 for movement between spaced-apart positions defined by the ratchet teeth 424. Each fixation block 430 may have a pair of openings 431 configured to receive fasteners (not shown) in installed positions in which outer end portions of the fasteners may be located within the openings 431. More specifically, the fasteners may be receivable in the fixation blocks 430 in installed positions in which their heads may rest in the openings 431 and their screw-threaded stems may project into vertebrae through the slots 421 in the bottom wall 420. In this arrangement, the bottom wall 420 may serve as a fixation plate in cooperation with the two movable fixation blocks 430. The slots 421 and the ratchet teeth 424 may permit the pairs of fasteners at the fixation blocks 430 to shift in relation to a corresponding pair of vertebrae to which the fixation blocks 430 are fastened by the fasteners.

A closure block 440 may be mounted on the base 412. A locking tab 442 on the cover 414 may snap into a slot 445 in the closure block 440 upon pivotal movement of the cover 414 from the open position shown in FIG. 14 to a closed position (not shown) in which it may be received over the base 412. This may be accomplished with an applied force in the same manner described above with reference to FIGS. 6-7. The cover 414 then may extend over the fastener heads on the fixation blocks 430 to serve as a retainer device that blocks the bone screws from backing out of their installed positions on the fixation devices 430.

The sizes, dimensions, and shapes of each of the above described fixation plates and other fixation assembly components may be varied to fit the anatomy of a given patient, depending at least in part on the size of the vertebra the plates will be attached to, and the size of the intervertebral space to be spanned. Fixation assemblies may also be substantially flat, to reduce the overall profile of the assemblies.

It is also expressly contemplated that each of the above described fixation assemblies may exhibit some or all of the suitable characteristics of each of the embodiments described herein. For instance, although not shown in a figure, it may be preferable to utilize the snap-down fastener retention device design of FIG. 13 with the box-shaped fixation assembly 410 of FIG. 14.

It is also expressly contemplated that each of the above described fixation assemblies may be assembled in a multi-level arrangement to span more than one intervertebral disc space. It is also contemplated that each of the above described assemblies may be assembled in corpectomy model, to span the length of at least one removed vertebral body. Variations or combinations of these alternatives is also contemplated.

Each of the fasteners, fixation plates, fastener retainers, and other components disclosed herein may be formed of a titanium alloy such as titanium-aluminum-niobium, which may be anodized. One material for use with each of the plates and screws described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners may also be burr free, with all sharp edges broken to a maximum of 0.1 mm.

It should be noted that the aforementioned descriptions and illustrations have been provided as examples of the configurations of translation plates that may be designed and assembled using the principles of the invention. These examples will be understood to one of ordinary skill in the art as being non-limiting in that a fixation assembly employing one or more of the disclosed features may be produced as desired or required for a particular patient's need. Thus, the features disclosed are "modular" in nature.

This written description sets forth the best mode of the claimed invention, and describes the claimed invention to enable a person of ordinary skill in the art to make and use it, by presenting examples of the elements recited in the claims. The patentable scope of the invention is defined by the claims themselves, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art which will embody the principles of the invention and fall within the spirit and the scope thereof.

The invention claimed is:

1. A fixation assembly for use with at least one bone fastener having a head, comprising:
    a fixation device having a first side flange, a second side flange, a first pair of openings, and a second pair of openings, each pair of openings located between the first side flange and the second side flange, each opening configured to receive at least a portion of a bone fastener, wherein each opening is configured to receive at least a portion of the head when the fixation device is implanted;
    a bone fastener retainer device having a top and bottom surface that is substantially continuous and without any apertures along the top surface that permit access to the openings in the fixation device receivable over the fixation device when the bone fastener retainer device and fixation device are brought in contact with one another in a closed position, wherein at least a portion of the bone fastener retainer device extends over at least a portion of the at least one opening when the fixation device is in the closed position;
    a pivot hinge comprising a hinge mechanism and a pin, the pivot hinge configured to permit the bone fastener retainer device to move between an open position wherein the bone fastener retainer device does not extend over at least a portion of the at least one opening and the closed position; and
    wherein the fixation device further comprises a closure block located between the first pair of openings and the second pair of openings and extending between and oriented substantially perpendicular to the first side flange and second side flange where the block further comprises a first integral locking structure, and the bone fastener retainer device further has a second integral locking structure on its bottom surface, the locking structures configured to engage each other in a locked condition when the bone fastener retainer device and fixation device are brought in contact with one another into the closed position.

2. The assembly of claim 1, wherein the first locking structure is a slot, and the second locking structure is a tab, and wherein the tab is receivable in the slot.

3. The assembly of claim 1, wherein the fixation device is a fixation plate, and the bone fastener retainer device is a cover plate.

4. The assembly of claim 1, wherein at least one opening is substantially slot-shaped and has a longitudinal axis.

5. The assembly of claim 4, wherein a bone fastener is allowed to translate along the longitudinal axis of the opening.

6. The assembly of claim 5, wherein the bone fastener is allowed to translate in situ.

7. The assembly of claim 5, wherein the bone fastener is allowed to translate after it has been at least partially inserted into a bone segment.

8. The assembly of claim 5, wherein the bone fastener is allowed to translate when the bone fastener retainer device is in a closed position.

9. The assembly of claim 1, wherein at least one opening is substantially circular.

10. A fixation assembly for use with a bone fastener, comprising:
    a fixation device having a length, a first side flange extending along the length and a second side flange extending along the length opposite the first side flange, a first pair of openings and a second pair of openings, each opening configured to receive at least a portion of a bone fastener in an installed position, and a rectangular shaped raised closure block being oriented substantially perpendicular to the length and extending between the first side flange and second side flange and between the first pair of openings and the second pair of openings the block further comprising a first locking structure, the bone fastener having a head, wherein at least a portion of the head is located within the opening when the fixation device is implanted;
    a bone fastener retainer device having a top and bottom surface and comprising a second locking structure within the bottom surface, the bone fastener retainer device receivable over the openings in the fixation device when the bone fastener retainer device and fixation device are brought in contact with one another in a closed position, wherein the portion of the bone fastener retainer device that extends over the openings when the fixation assembly is in the closed position is substantially continuous and without apertures that permit access to the openings in the fixation device; and
    a first hinge wherein the fixation device is fixedly attached to the bone fastener retainer device, and configured to permit the bone fastener retainer device to move between an open position wherein the bone fastener retainer device does not extend over at least a portion of the at least one opening and the closed position.

11. The assembly of claim 10, wherein the fixation device is a fixation plate, and the bone fastener retainer device is a cover plate.

12. The assembly of claim 10, wherein at least one opening is substantially slot-shaped and has a longitudinal axis.

13. The assembly of claim 12, wherein a bone fastener is allowed to translate along the longitudinal axis of the opening.

14. The assembly of claim 13, wherein the bone fastener is allowed to translate in situ.

15. The assembly of claim 13, wherein the bone fastener is allowed to translate after it has been at least partially inserted into a bone segment.

16. The assembly of claim 13, wherein the bone fastener is allowed to translate when the bone fastener retainer device is in a closed position.

17. The assembly of claim 10, wherein at least one opening in substantially circular.

18. The assembly of claim 10 further comprising a pivot hinge which comprises a hinge mechanism and a pin.

* * * * *